US009610399B2

(12) United States Patent
Gomez

(10) Patent No.: US 9,610,399 B2
(45) Date of Patent: *Apr. 4, 2017

(54) INTRAVENOUS POLE SYSTEM

(71) Applicant: David Julian Gomez, Raleigh, NC (US)

(72) Inventor: David Julian Gomez, Raleigh, NC (US)

( * ) Notice: Subject to any disclaimer, the term of this patent is extended or adjusted under 35 U.S.C. 154(b) by 63 days.

This patent is subject to a terminal disclaimer.

(21) Appl. No.: 14/301,972

(22) Filed: Jun. 11, 2014

(65) Prior Publication Data

US 2014/0361129 A1    Dec. 11, 2014

Related U.S. Application Data

(60) Provisional application No. 61/833,721, filed on Jun. 11, 2013.

(51) Int. Cl.
*A47G 23/02* (2006.01)
*A61M 5/14* (2006.01)

(52) U.S. Cl.
CPC .................. *A61M 5/1415* (2013.01)

(58) Field of Classification Search
CPC .............. A61M 5/1414; A61M 5/1415; A61M 5/1417; A61M 5/14; A61M 2209/08; A61M 2209/082; A61M 2209/084; F16M 11/42
USPC .................................................. 248/128–129
See application file for complete search history.

(56) References Cited

U.S. PATENT DOCUMENTS

| 5,110,076 | A | * | 5/1992 | Snyder | A61M 5/1415 248/125.3 |
|---|---|---|---|---|---|
| 5,188,323 | A | * | 2/1993 | David | A61M 5/1415 248/125.1 |
| 5,556,065 | A | * | 9/1996 | Wadley | A61G 12/008 248/129 |
| 6,991,495 | B1 | * | 1/2006 | Aromin | H01H 83/14 361/42 |
| 7,731,136 | B1 | * | 6/2010 | Chisolm | A61M 5/1415 211/204 |
| 9,295,743 | B2 | * | 3/2016 | Gomez | A61L 2/10 |
| 2008/0116157 | A1 | * | 5/2008 | Fulbrook | A61M 5/1415 211/60.1 |
| 2008/0156946 | A1 | * | 7/2008 | Schmutzer | A61M 5/1415 248/125.8 |
| 2009/0046402 | A1 | * | 2/2009 | Malkus | H01R 25/003 361/87 |
| 2009/0156061 | A1 | * | 6/2009 | Bernstein | H01R 13/652 439/652 |
| 2009/0261215 | A1 | * | 10/2009 | Lambert | A61M 5/1415 248/125.8 |
| 2013/0168526 | A1 | * | 7/2013 | Walther | A61M 5/1415 248/519 |
| 2014/0132207 | A1 | * | 5/2014 | Fisher | H02J 7/0052 320/108 |

\* cited by examiner

*Primary Examiner* — Christopher E Garft
(74) *Attorney, Agent, or Firm* — Phillips Lytle LLP; David L. Principe

(57) ABSTRACT

An intravenous pole with individually adjustable ring support members, a freely rotating slip ring with a plurality of electrical plug receptacles, and a wireless recharging system.

20 Claims, 6 Drawing Sheets

INTRAVENOUS POLE SYSTEM

CROSS-REFERENCE TO RELATED APPLICATION

The present application claims priority benefit of U.S. Provisional Patent Application No. 61/833,721, entitled "Intravenous Pole" filed on Jun. 11, 2013.

TECHNICAL FIELD

The present invention relates generally to the field of devices for hospitals and medical facilities, and more particularly to an intravenous pole system.

BACKGROUND OF THE INVENTION

Standard IV poles are typically telescopic in nature and rely on a tension screw/handle system or a rotating friction ring to adjust the IV hanging apparatus. This arrangement is always a two-handed method and after some service use, this tension based system usually fails to hold the pole in the correct position. There have even been instances where the weight of the IV fluids has caused the telescopic arrangement to collapse causing injury to both patients and care providers.

There are many articles supporting the rise of hospital acquired infections coming from high tough surface areas in clinical areas and especially in the operating room and intensive care unit environments. The current IV pole designs have multiple non-linear surface areas that are difficult to clean.

The IV pole is intended to hold IV pumps that must be plugged into an outlet for operation. In the operating room there are also many other products that utilize a simple power strip addition to the pole. In the operating room, the use of fluid warmers and warm air blowing devices that warm patients during surgery are necessary and must use local receptacle outlets. Sometimes the IV pole power strips are used for other devices in the operating room necessary for surgery. These designs are cumbersome. They are in a fixed position in relation to the devices plugged into them. As the IV pole must be freely movable and adjusted in relation to the operating room table or bed, this fixed receptacle position causes a tethering effect which is difficult to position with multiple fixed plugged wire projection points. This arrangement also causes a significant tripping hazard.

Accordingly, there is a need for an IV pole with individually, one-hand adjustable rings for supporting different IV bags with different volume and flow requirements. There is also a need for an improved electrical system that provides greater versatility and flexibility and that provides for providing power from a first IV pole to a second IV pole. There is also a need for a base for an IV pole having a unique shape with clean lines and minimal surface areas and with the casters protected from contamination, for promoting infection control.

BRIEF SUMMARY OF THE INVENTION

With parenthetical reference to the corresponding parts, portions or surfaces of the disclosed embodiment, merely for the purposes of illustration and not by way of limitation, the present invention meets the above described needs by providing an intravenous pole (10) for use in supporting a plurality of fluid bags (35). A base (55) has a hub (56) disposed in a central portion of the base (55). The base (55) has a top surface (64) extending laterally from the hub (56). The base (55) has an opening (58, 61) extending inward from a perimeter of the top surface (64) toward the hub (56). The top surface (64) of the base (55) also covers at least one caster (57).

The pole (10) has a lower end secured to the hub (56) of the base (55). The pole (10) has a lower section with a receptacle housing (40) disposed thereon. The pole (10) has an upper section with multiple channels defined therein. More than one of the channels has a plurality of openings (22) defined along its longitudinal axis. More than one of the channels is configured to receive a ring support member (19a-d) therein. The ring support member (19a-d) has a body portion (25a-d), and a lateral portion (28a-d). The lateral portion (28a-d) has a ring disposed thereon for receiving at least one of the plurality of fluid bags (35).

A retractable pin (38) is disposed on the ring support member (19a-d) such that the pin (38) moves between a first position where it is inserted into one of the openings (22) in the upper section of the pole (10) and a second position where it is removed from the opening (22).

A plurality of electrical plug receptacles (43a-f) are mounted in the receptacle housing (40).

In another embodiment, the system may further comprise a rechargeable battery (212) positioned toward the bottom of a pole (200) so that it can be wirelessly recharged by means of source resonator pads (215) positioned in the floor (218) of a healthcare facility.

DESCRIPTION OF THE PREFERRED EMBODIMENTS

Figure 1:
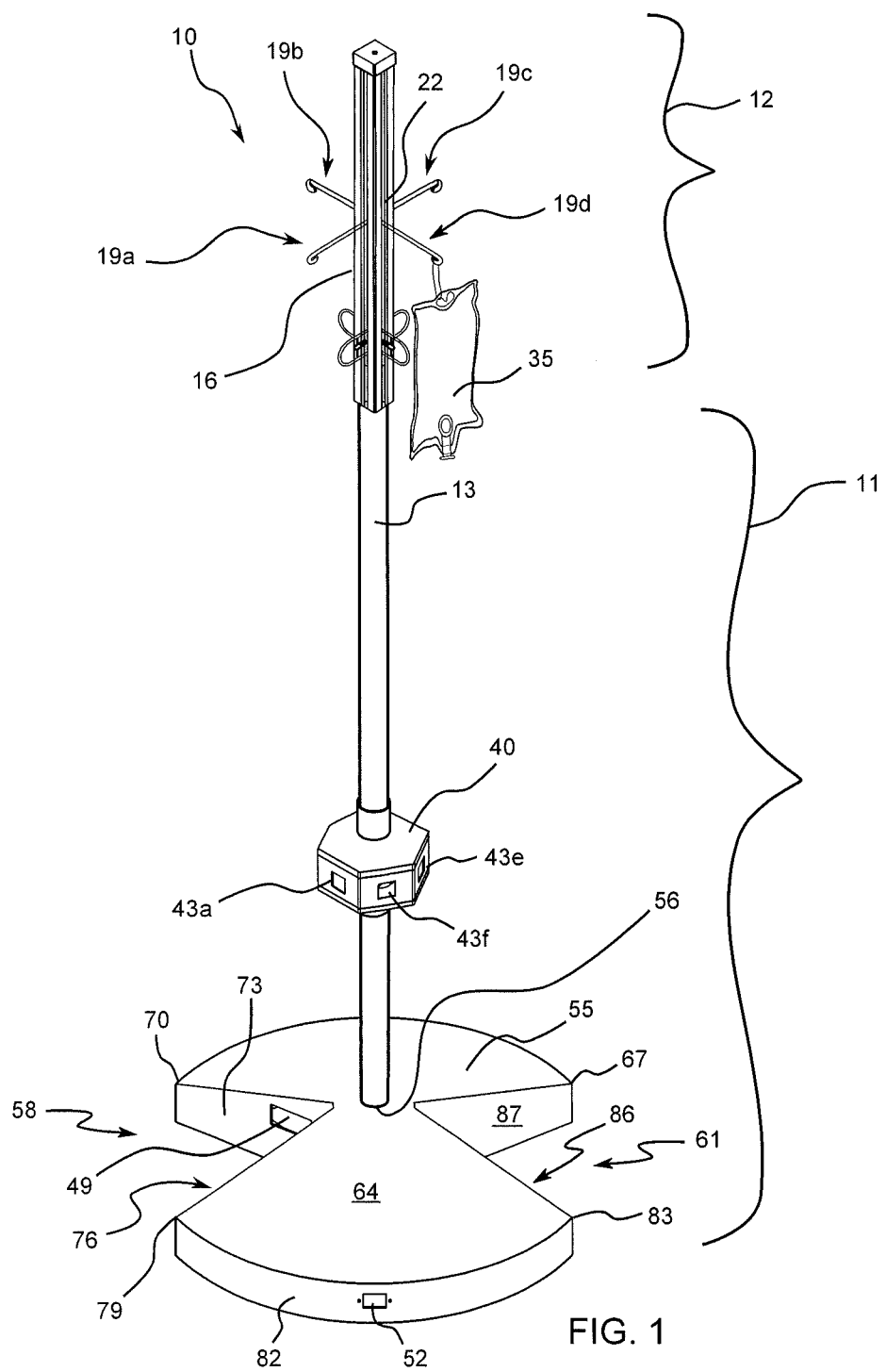
FIG. 1 is a front perspective view of one embodiment of the intravenous pole.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Figure 5:
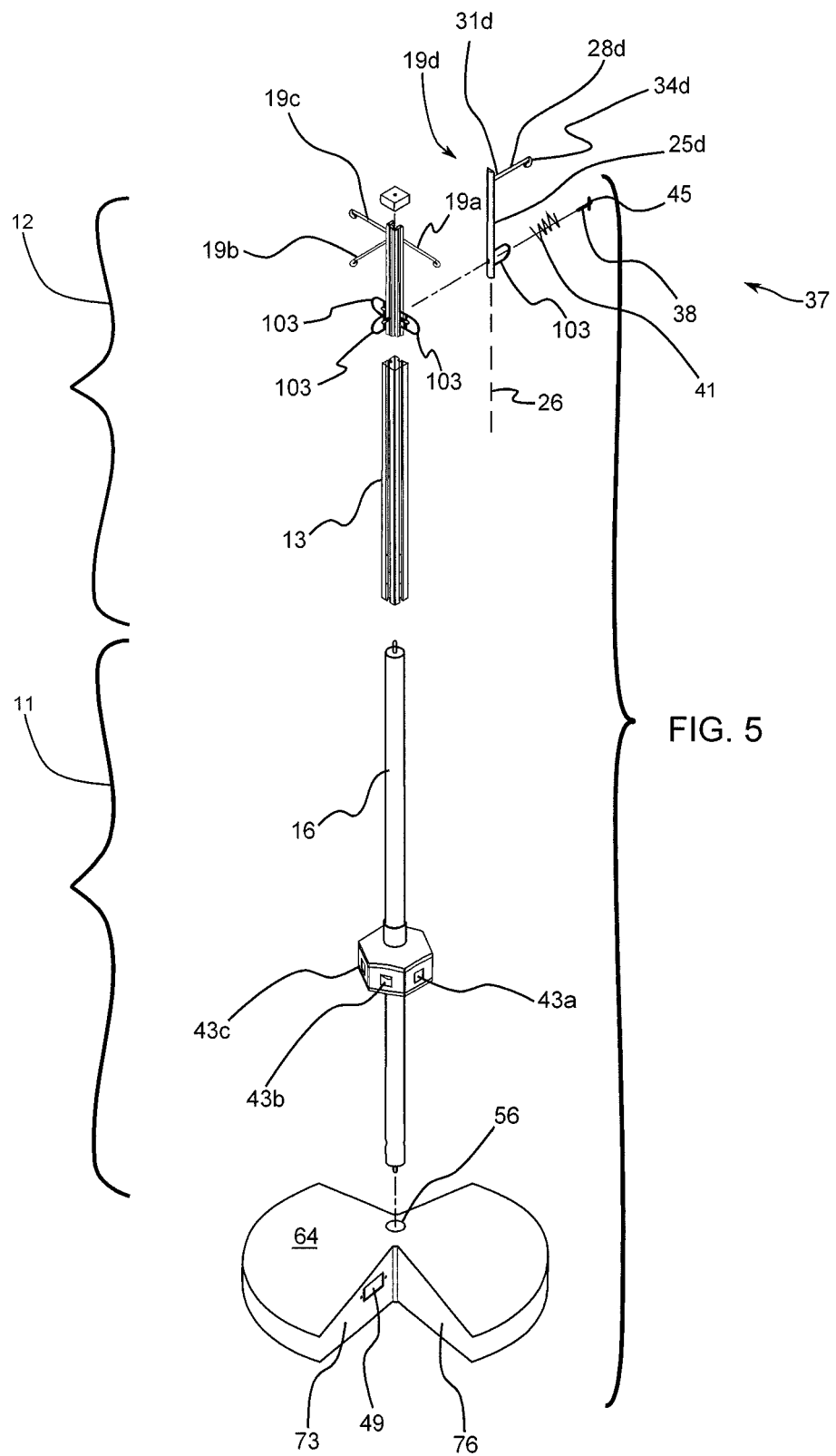
FIG. 5 is an exploded view thereof.

As shown in FIG. 1, an intravenous pole 10 may have a lower section 11 with a support member 13 that receives central support member 16 and a plurality of individually adjustable ring support members 19a, 19b, etc. forming an upper section 12. The lower and upper sections 11, 12 may be integrally formed or may be formed by separate members. The central support member 16 may be fixed relative to the support member 13, and support member 16 includes a plurality of apertures 22 along the length thereof. Turning to FIG. 5, ring support member 19c includes a body portion 25c and a lateral portion 28c. The lateral portion 28c extends transverse to the longitudinal axis 26 of the body portions 25c. The lateral portion 28c has a proximal portion 31c that is disposed adjacent to the body portion 25c, and the lateral portion 28c has a distal portion 34c. The distal portion 34c is curled to provide a hook for attaching a bag 35 (FIG. 1) of intravenous fluids to the intravenous pole 10.

Returning to FIG. 1, a receptacle housing 40 may be rotatably mounted to support member 13. The receptacle housing 40 may have a hexagonal shape with a snap-in outlet 43a-f disposed on each of the six sides. The snap-in outlets 43a-f may be rated for 15 amps. The combination of the hexagonal shaped housing 40 and the rotatable mounting of the housing 40 provides for a wide range of angles and direction for providing power to additional devices. The outlets 43a-f are set in the pole 10 and are not able to be removed from the pole 10. This arrangement is designed to replace the use of consumer power strips attached to an intravenous pole as is common in the industry. Power for the pole 10 may be provided from a cord that may contain a C13 plug on the end of it that may plug into a C14 receptacle 46 on the base of the pole 10. Power may also be provided by batteries including rechargeable batteries or the like. The power from the base is fed to the outlets disposed in the housing 40.

Another aspect of the electrical design of the present invention is the ability to distribute power to a second intravenous pole. The system of the present invention also includes a ground fault circuit interrupter 49 (GFCI). If the GFCI registers an irregularity in the incoming and outgoing current it will cut the connection of the circuit preventing any damage to equipment connected to the circuit.

Figure 7:
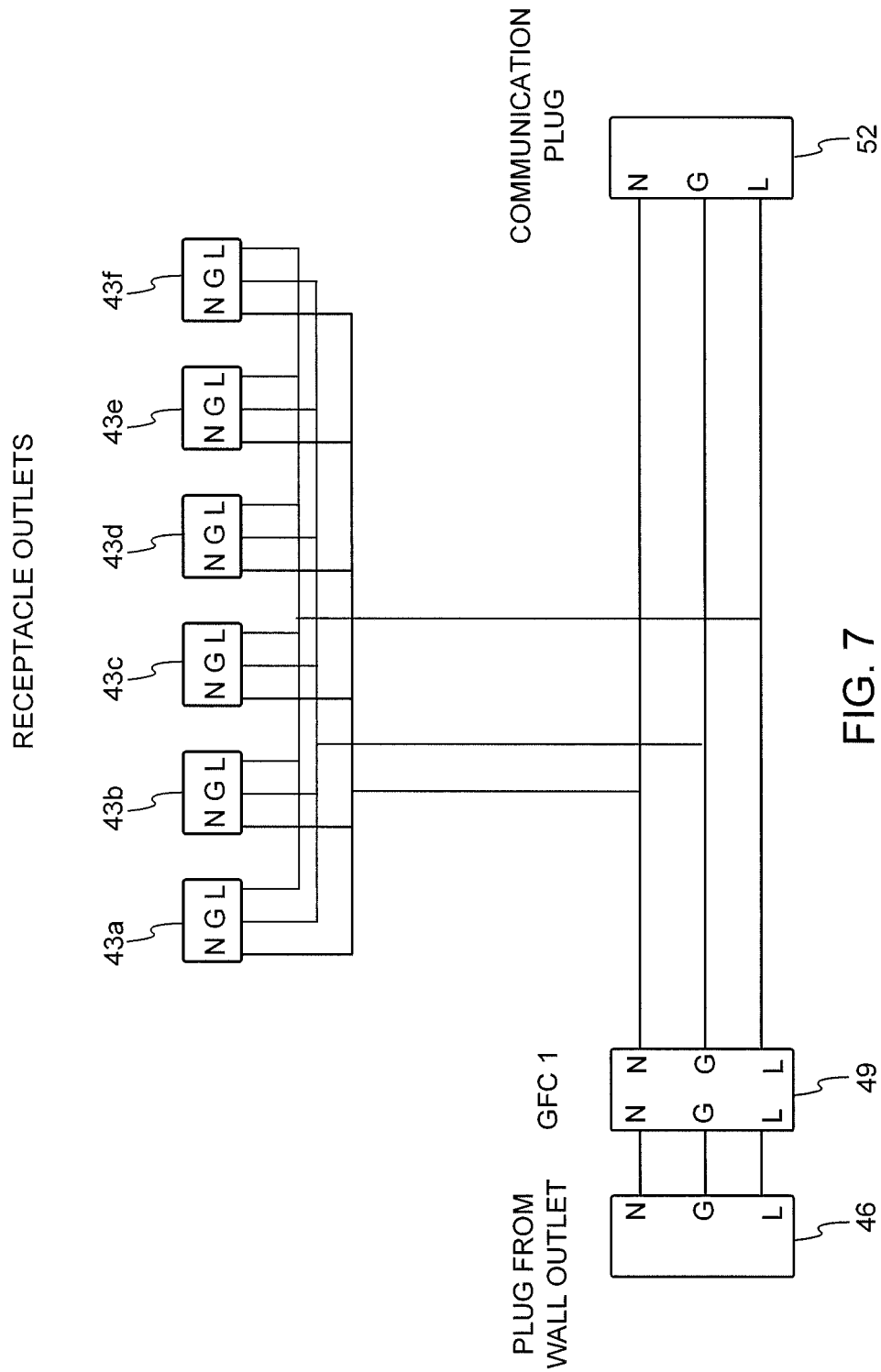
FIG. 7 is an electrical diagram for one embodiment of the invention.

As shown in FIG. 7, the outlets 43a-f may be wired in parallel such that the total current that the pole 10 could handle is theoretically 90 amps. (15 amps per outlet times six). The outlet 52 may be rated at 20 amps and may provide power to another pole by connecting an electrical cord leading to the other pole.

In FIG. 1, a base 55 is connected at its hub 56 to the pole 10 toward the bottom of the support member 13. The base 55 may have an overall shape that is curved with a pair of centrally located pie-shaped openings 58 and 61. The gap created by the openings 58, 61 allows the IV pole 10 to be moved closer to fixed objects, staff, and mobile machinery in the operating room or intensive care unit.

The top surface 64 of the base 55 covers casters 57 (FIG. 2) and extends downwardly and outwardly from the hub 56 to a point 67 disposed adjacent to the opening 61. The surface 64 is curved from point 67 to a point 70 on the opposite side of the base 55. From point 70, the surface 64 extends inward adjacent to opening 58. Opening 58 is bordered at the top by surface 64 and is bordered by inner faces 73 and 76. The GFCI 49 may be disposed on inner surface 73. The surface 64 extends to another point 79 disposed adjacent to opening 58. As shown at the bottom of the figure, an outer surface 82 includes an outlet 52 for connecting power to another pole 10. On the opposite side of the base 55, a power cord with an electrical plug or a receptacle 46 for receiving an AC cord may be provided for receiving power from a wall outlet. The surface 64 extends to point 83 adjacent to opening 61. Opening 61 is bordered by faces 86, 87.

Figure 2:
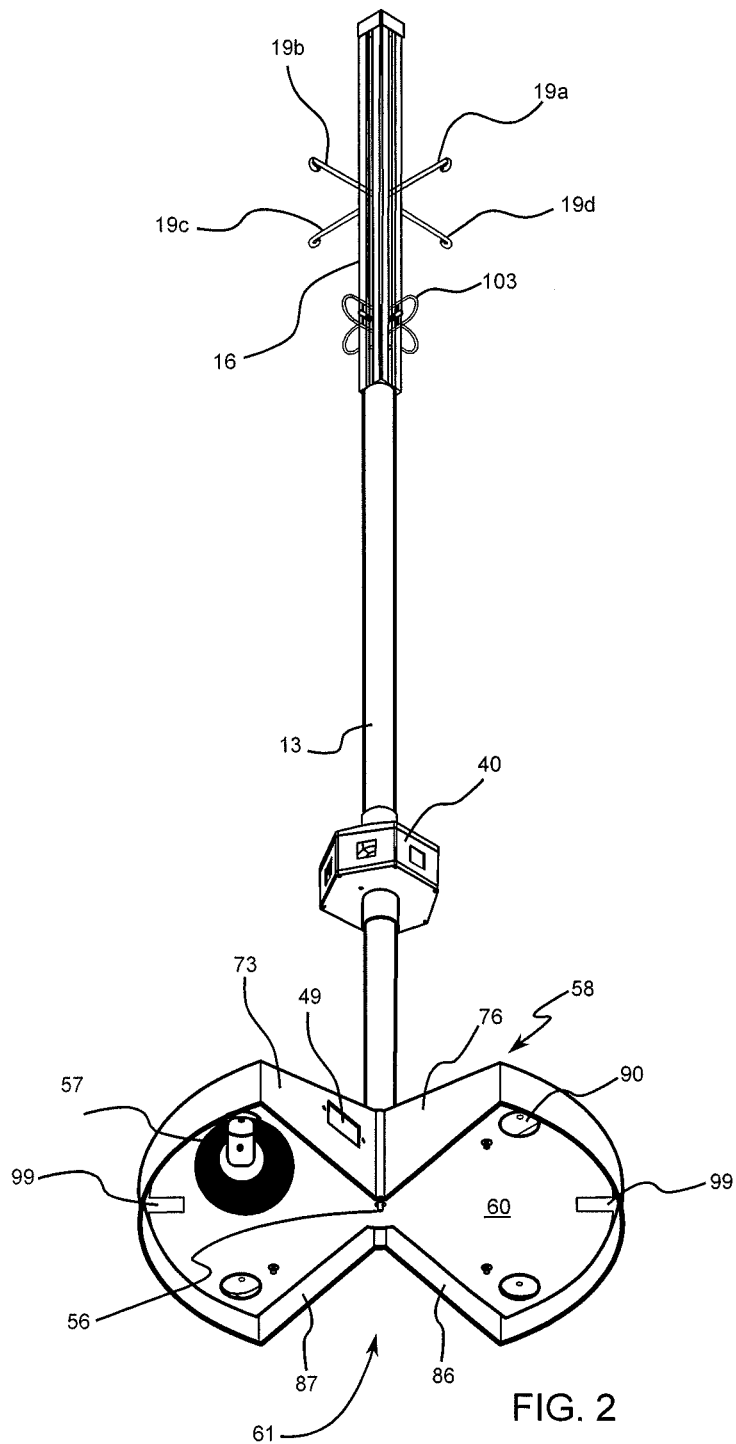
FIG. 2 is another perspective view of the embodiment shown in FIG. 1.

Turning to FIG. 2, the underside of the base 55 is shown with all but one of the casters 57 removed for clarity. The bottom surface 60 of the base 55 extends laterally about the hub 56. Cutouts 90 may be provided for mounting casters 57, and recessed portions 99 may be provided for mounting electrical receptacles 46 and 52.

Figure 3:
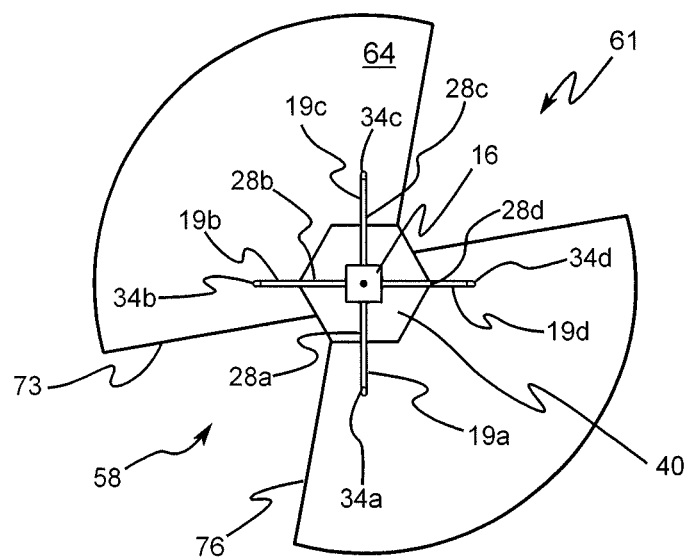
FIG. 3 is a top plan view of the embodiment shown in FIG. 1.

In FIG. 3, the central support member 16 is shown with ring support members 19a, 19b, 19c and 19d attached to different faces of member 16. The ring support members 19a-d each have lateral portions 28a-d that extend to distal portions 34a-d for supporting bags containing intravenous fluids. Each of the ring support members 19a-19d may be individually adjusted.

Figure 4:
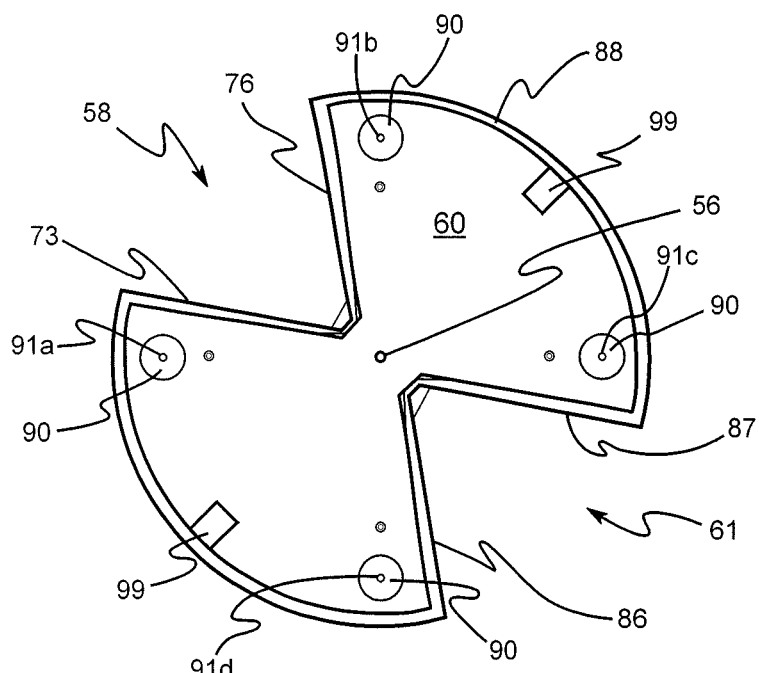
FIG. 4 is a bottom plan view thereof.

In FIG. 4, the housing 88 for the base 55 is shown in greater detail. The base 55 includes four mounting positions 91a-d for receiving casters (not shown). The casters provide for rolling the intravenous pole 10 across the floor or other supporting surface. The base 55 includes recessed portions 99 for receiving the inlet and outlet power. The incoming power comes from a wall outlet and provides a source of AC power to the pole. The outlet provides for connecting another pole to pole 10 to receive power.

Turning to FIG. 5, an exploded view shows the operation of the ring support members 19a-d in greater detail. Each side of the central support member 16 may be provided with a T-shaped slot for receiving the body portions 25a-d of the ring support members 19a-d, respectively. The slots are bordered by openings 22 disposed along the longitudinal axis of the body portions 25a-d. As shown with respect to ring support member 19d, a retractable pin 38 may be inserted into an opening 22 to fix the position of the ring support member 19d relative to the central support member 16. The pin 38 may be spring biased into the opening 22 such that once the pin 38 is inserted into the opening 22 it remains there until it is removed against the force of the spring 41. An oval shaped member 103 may be provided for easy one handed adjustment of the ring support member 19d. With one hand, the oval shaped member 103 may be grasped while simultaneously pulling the pin 38 against the force of the spring 41 to retract it from one of the openings 22. With the pin 38 removed, the ring support member 19d can be slid in either direction along the longitudinal axis of the central support member 16. When the pin 38 is aligned with another one of the openings and is released from the grip of the user, the pin 38 will slide into the aligned opening under the force of the spring 41. Accordingly, each individual ring support member 19a-d may be individually adjusted with a simple one handed operation.

As shown in FIG. 5, the central support member 16 is disposed in the center of a plurality of ring support members 19a, 19b, 19c, 19d. Each ring support member 19a-d, may be individually adjusted to raise and lower its attached hook. The height of the hook may thereby be adjusted to accommodate different sized fluid bags and different gravity based flow rates. One embodiment of an adjusting mechanism 37 is shown. The adjusting mechanism 37 includes a pin 38 that is biased by a spring 41. The pin 38 includes a head 45 that can be gripped by one hand. At the opposite end from the head 45, a distal end 47 of the pin 38 is sized to fit into one of the plurality of apertures 22. When the head 45 is released, the spring 41 biases the distal end 47 into the aperture 22 such that the ring support member 19d is fixed into a position relative to the support member 16. If the user wants to adjust the height of the ring support member 19b, the user may grip the head 45 with one hand to pull rightwardly with respect to the orientation of FIG. 5, Once the distal end 47 is retracted from the opening 22 against the force of the spring 41, the ring support member 19b can be lifted upward or lowered downward until the distal end 47 aligns with another one of the apertures 22. Once the ring support member 19c is repositioned, the user can release the head 45 and the spring 41 will urge the distal end 47 into engagement with the aligned aperture 22 to lock the support member 19d into position.

Figure 6:
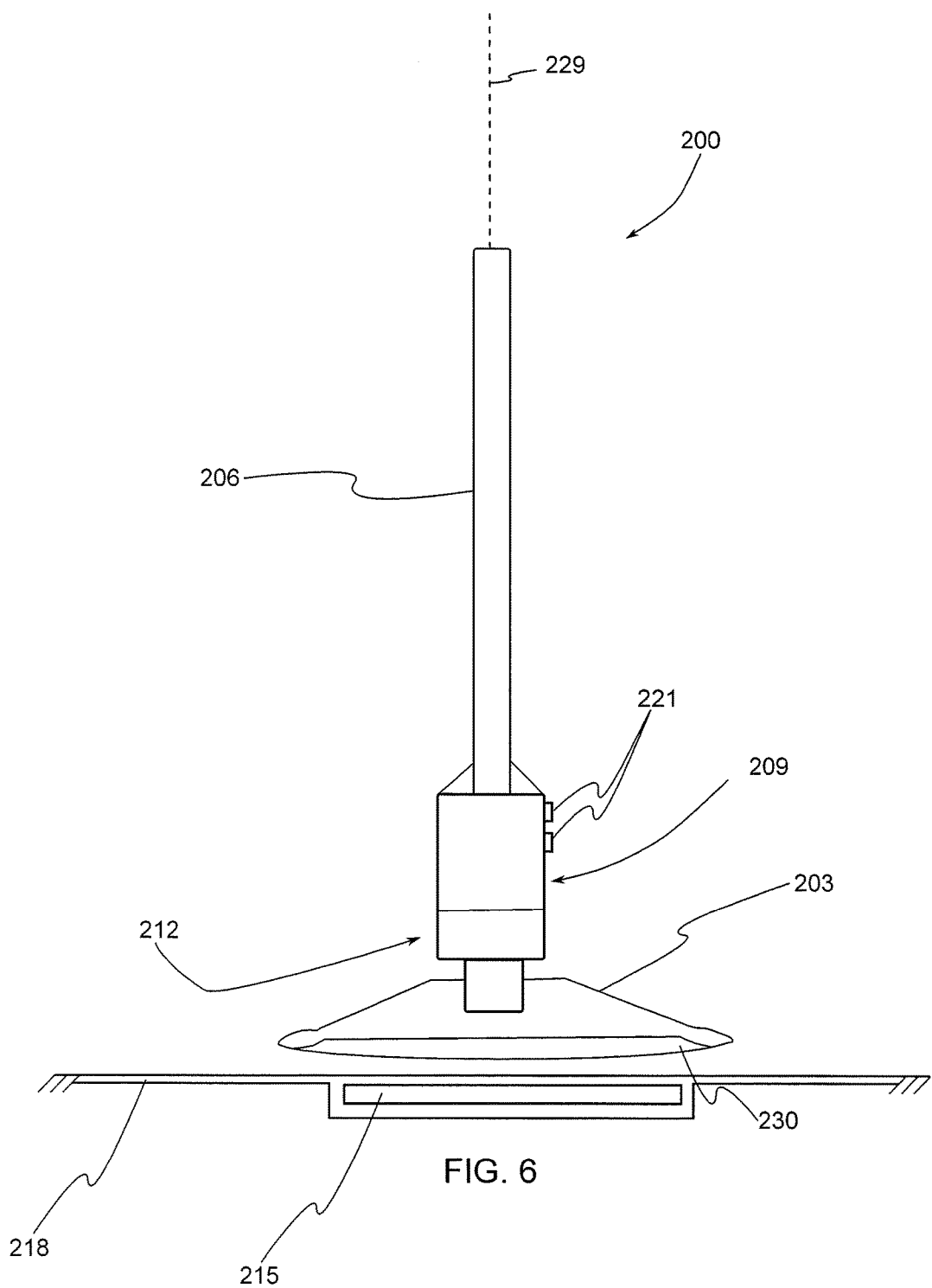
FIG. 6 is a front elevational view of an alternate embodiment of the invention.

In FIG. 6, another embodiment of the invention is shown. IV pole 200 includes a base 203, a central pole shaft 206, a rotating slip ring 209 and a rechargeable battery 212. The rechargeable battery 212 is positioned toward the bottom of the IV pole 200 so that it can be recharged by means of source resonator pads 215 positioned in the floor 218 of the facility. The wireless transfer of power from a power source to a capture device such as a rechargeable battery 212 is known to those of ordinary skill in the art and is commercially available from companies such as Witricity Corporation of Watertown, Mass. Wireless energy transfer systems are disclosed in U.S. Pat. Nos. 7,741,734; 7,825,543; 8,022,576; 8,035,255; 8,076,800; 8,076,801; 8,084,889; 8,097,983; 8,106,539; 8,115,448; 8,304,935; 8,400,017; 8,400,018; 8,400,019; 8,400,020; 8,400,021; 8,400,022; 8,400,023; and 8,400,024; which are hereby incorporated by reference. When the IV pole 200 is in place over the resonator pad 215 the charging station trickle charges the battery 212 which in turn powers the entire pole and its powered utility devices. The IV pole shaft 206 itself is a magnetic resonating DC power source that may trickle charge batteries of IV pole mounted devices allowing their use without plugging them into native room receptacles. The capture device for receiving the charge from the IV pole shaft 206 may be incorporated directly into the device such as an IV pump or may be integrated into a clamp apparatus used to hold the IV pump onto the IV pole shaft 206.

The rotating slip ring 209 provides a plurality of receptacles 221 to rotate three hundred sixty degrees about the longitudinal axis 229 of the IV pole shaft 206. The slip ring 209 carries a plurality of receptacles 221. The free rotating slip ring receptacle unit 209 may also house a rechargeable battery 212 that powers devices such as, but not limited to, a Bair hugger, fluid warmer, or IV pump, for extended amounts of time.

The IV pole 200 of the present invention eliminates the main power cord serving the entire pole battery/power system. The IV pole 200 includes a base system on wheels directly above the floor with an integral battery 212 sized to provide power for all medical items plugged into the top of the IV pole system. The base of the IV pole includes a capture device 230 that allows the base of the pole to be charged from strategically placed source resonator pads 215 located in the floor 218 of a hospital. Using an RF amplifier and a grid layout of source resonators (i.e., that is wireless power sources) a portable IV pole 200 capable of providing power to IV pumps may be provided without the need for an AC power cord. The retrofit of the hospital floor to include the source resonator pads 215 is a minor and fairly non-intrusive operation that can be accomplished without compromising the sterility and clean-room environment of the hospital spaces.

The present invention contemplates that many changes and modifications may be made. Therefore, while the presently-preferred form of the emissions measuring system has been shown and described, and several modifications and alternatives discussed, persons skilled in this art will readily appreciate that various additional changes and modifications may be made without departing from the spirit of the invention, as defined and differentiated by the following claims.

The invention claimed is:

1. An intravenous pole system for use in supporting a plurality of fluid bags, the system comprising:
   a base having a hub disposed in a central portion, the base having a top surface extending laterally from the hub, the top surface extending downwardly and outwardly from the hub, the base having an opening extending inward from a perimeter of the top surface toward the hub, wherein the opening comprises a pair of openings disposed on opposite sides of the base, the top surface of the base covering at least one caster;
   a pole having a lower end secured to the hub of the base, the pole having a lower section with a receptacle housing disposed thereon, wherein the receptacle housing rotates freely about the pole, the pole having an upper section with multiple channels defined therein, more than one of the channels having a plurality of openings defined along its longitudinal axis, more than one of the channels configured to receive a ring support member therein, the ring support member having a body portion, and a lateral portion, the lateral portion having a ring disposed thereon for receiving at least one of the plurality of fluid bags;
   a retractable pin disposed on the ring support member such that the pin moves between a first position where the pin is inserted into one of the openings in the upper section of the pole and a second position where it is removed from one of the openings in the upper section of the pole; and,
   a plurality of electrical plug receptacles mounted in the receptacle housing.

2. The intravenous pole system of claim 1, wherein the base further comprises a power outlet for distributing power to a second intravenous pole.

3. The intravenous pole system of claim 1, wherein the receptable housing has a hexagonal shape.

4. The intravenous pole system of claim 1, wherein the retractable pin is acted on by a biasing member.

5. The intravenous pole system of claim 1, further comprising a handle disposed adjacent the retractable pin.

6. The intravenous pole system of claim 1, further comprising a ground fault circuit interrupter (GFCI).

7. The intravenous pole system of claim 1, wherein more than one ring support member may be adjusted to a different height on the pole.

8. The intravenous pole system of claim 1, wherein the base has an opening extending from the perimeter of the top surface toward the hub on at least two sides of the base.

9. An intravenous pole system for use in supporting a plurality of fluid bags and for use to supply power to a second intravenous pole disposed in its vicinity, the system comprising:
   a base having a hub disposed in a central portion, the base having a top surface extending laterally from the hub, the top surface extending downwardly and outwardly from the hub, the base covering at least one caster, the base having two or more openings extending inward from a perimeter of the top surface toward the hub, the base having a power inlet for receiving incoming power and having a power outlet for distributing power to the second intravenous pole;

a pole having a lower end secured to the hub of the base, the pole having a lower section with a receptacle housing rotatably disposed thereon, wherein the receptacle housing rotates freely about the pole, the pole having an upper section with multiple channels defined therein, more than one of the channels having a plurality of openings defined along its longitudinal axis, more than one of the channels configured to receive a ring support member therein, the ring support member having a body portion, and a lateral portion, the lateral portion having a ring disposed thereon for receiving at least one of the plurality of fluid bags;

a retractable pin disposed on the ring support member such that the pin moves between a first position where the pin is inserted into one of the openings in the upper section of the pole and a second position where it is removed from one of the openings in the upper section of the pole;

a biasing member configured to urge the retractable pin into one of the openings in the upper section of the pole when the pin is disposed in alignment with the opening; and, a plurality of electrical plug receptacles mounted in the receptacle housing.

10. The system of claim 9, wherein the top surface of the base has a round shape with two pie-shaped sections removed.

11. The system of claim 9, wherein the receptacle housing has a hexagonal shape.

12. The system of claim 9, wherein the pole further comprises a rechargeable battery.

13. The system of claim 12, further comprising a source resonator pad disposed in a support surface adjacent to the pole such that the rechargeable battery is wirelessly charged.

14. The system of claim 9, further comprising a ground fault circuit interrupter (GFCI).

15. An intravenous pole system for use in supporting a plurality of fluid bags, the system comprising:

a base having a hub disposed in a central portion, the base having a top surface extending laterally from the hub, the top surface extending downwardly and outwardly from the hub, the base having an opening extending inward from a perimeter of the top surface toward the hub, the top surface of the base covering at least one caster;

a pole having a lower end secured to the hub of the base, the pole having a lower section with a receptacle housing disposed thereon, wherein the receptacle housing rotates freely about the pole, the pole having an upper section with multiple channels defined therein, more than one of the channels having a plurality of openings defined along its longitudinal axis, more than one of the channels configured to receive a ring support member therein, the ring support member having a body portion, and a lateral portion, the lateral portion having a ring disposed thereon for receiving at least one of the plurality of fluid bags;

means for adjusting the position of the ring support member relative to the upper section of the pole;

a plurality of electrical plug receptacles mounted in the receptacle housing.

16. The intravenous pole system of claim 15, wherein the base further comprises a power outlet for distributing power to a second intravenous pole.

17. The intravenous pole system of claim 15, wherein the receptable housing has a hexagonal shape.

18. The intravenous pole system of claim 15, wherein the adjusting means comprises a retractable pin acted on by a biasing member.

19. The intravenous pole system of claim 1, wherein the base is dome-shaped.

20. The intravenous pole system of claim 15, wherein the base is dome-shaped.

* * * * *